(12) United States Patent
Sweet et al.

(10) Patent No.: US 10,215,674 B2
(45) Date of Patent: Feb. 26, 2019

(54) DEVICE FOR MEASURING THE DYNAMIC STRESS/STRAIN RESPONSE OF DUCTILE MATERIALS

(71) Applicant: The Boeing Company, Chicago, IL (US)

(72) Inventors: William J. Sweet, Seattle, WA (US); Kevin Richard Housen, Tacoma, WA (US); Arthur C. Day, Seattle, WA (US); Jason Scott Damazo, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 253 days.

(21) Appl. No.: 15/211,891

(22) Filed: Jul. 15, 2016

(65) Prior Publication Data

US 2018/0017475 A1 Jan. 18, 2018

(51) Int. Cl.
*G01N 3/307* (2006.01)
*G01N 3/04* (2006.01)
*G01N 3/30* (2006.01)

(52) U.S. Cl.
CPC .............. *G01N 3/307* (2013.01); *G01N 3/04* (2013.01); *G01N 3/30* (2013.01); *G01N 2203/001* (2013.01); *G01N 2203/0017* (2013.01); *G01N 2203/0035* (2013.01); *G01N 2203/0055* (2013.01); *G01N 2203/0094* (2013.01); *G01N 2203/0098* (2013.01); *G01N 2203/0252* (2013.01); *G01N 2203/0278* (2013.01); *G01N 2203/0647* (2013.01); *G01N 2203/0676* (2013.01)

(58) Field of Classification Search
CPC ...................................................... G01N 3/307
See application file for complete search history.

(56) References Cited

U.S. PATENT DOCUMENTS

| 6,109,093 A | 8/2000 | Albertini et al. |
| 6,848,321 B2 | 2/2005 | Bossi et al. |
| 7,024,922 B1 | 4/2006 | Nakagawa et al. |

(Continued)

FOREIGN PATENT DOCUMENTS

| CN | 203643279 U | 6/2014 |
| CN | 104678853 A * | 6/2015 |

OTHER PUBLICATIONS

Split Hopkinson Pressure Bar Brochure; High Strain Rate Material Testing, www.relinc.net; 2012; 6 pgs.

(Continued)

*Primary Examiner* — Clayton E. LaBalle
*Assistant Examiner* — Dennis Hancock
(74) *Attorney, Agent, or Firm* — MH2 Technology Law Group LLP

(57) ABSTRACT

A method and apparatus for measuring a dynamic tensile stress and/or tensile strain response of a material such as an elastic material and/or a ductile material. The apparatus may include a striker bar, a stretcher bar, and a drive assembly configured to propel the striker bar toward the stretcher bar. The apparatus may further include a stationary specimen mount and a movable specimen mount that receive a test sample. The striker bar and the stretcher bar of the apparatus may provide a continuous stress on the test sample and an accurate tensile stress/strain measurement.

20 Claims, 8 Drawing Sheets

(56) References Cited

U.S. PATENT DOCUMENTS

| | | | |
|---|---|---|---|
| 7,159,470 | B2 | 1/2007 | Saguto |
| 7,392,708 | B2 | 7/2008 | Bohlmann et al. |
| 8,250,928 | B2 | 8/2012 | Miller et al. |
| 8,347,747 | B2 | 1/2013 | Clingman et al. |
| 8,527,218 | B2 | 9/2013 | Georgeson et al. |
| 8,616,068 | B2 | 12/2013 | Miller et al. |
| 8,645,086 | B1 | 2/2014 | Castle et al. |
| 9,063,032 | B2 | 6/2015 | Appuhamillage et al. |
| 9,261,444 | B1 | 2/2016 | Sutherland et al. |
| 9,778,157 | B2 * | 10/2017 | MacDougall ............ G01N 3/30 |
| 2015/0308932 | A1 * | 10/2015 | Whittington ........... G01N 3/062 73/760 |

OTHER PUBLICATIONS

Yokoyama et al., "Determination of the Impact Tensile Strength of Structural Adhesive Butt Joints with a Modified Split Hopkinson Pressure Bar," International Journal of Adhesion and Adhesives, vol. 56, Jan. 1, 2015, pp. 13-23.

Extended European Search Report dated Nov. 30, 2017 in corresponding EP Application 17180769.6, 10 pages.

* cited by examiner

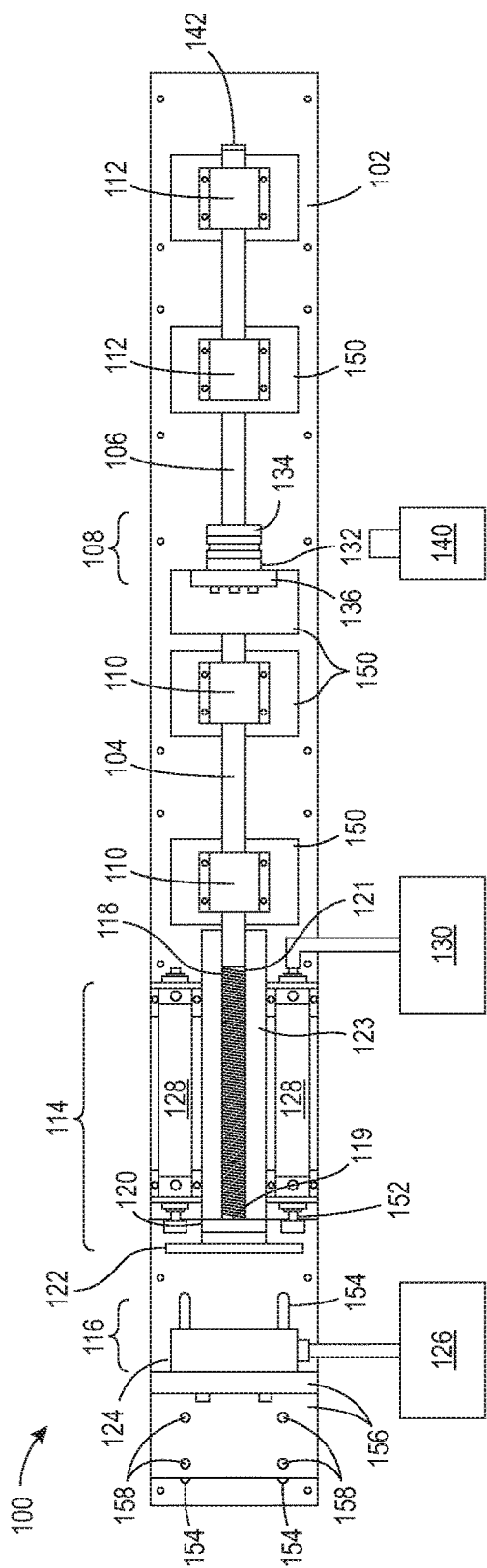
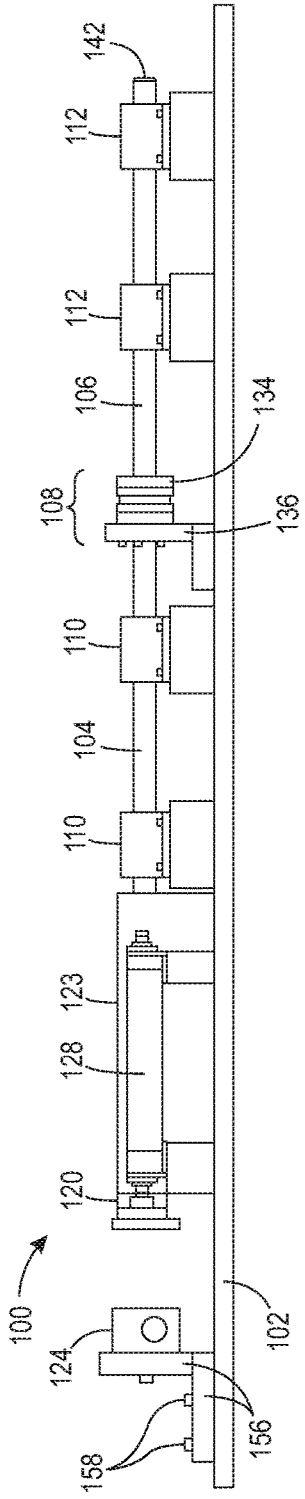
FIG. 2
FIG. 3

DEVICE FOR MEASURING THE DYNAMIC STRESS/STRAIN RESPONSE OF DUCTILE MATERIALS

TECHNICAL FIELD

The present teachings relate to the field of materials metrology and, more particularly, to a device for measuring stress and strain characteristics of a flexible pliable material or another material.

BACKGROUND

This section provides background information related to the present disclosure which is not necessarily prior art.

The design and manufacture of a structure requires the selection of appropriate materials for structural components or device substructures. To select a suitable material, scientists, engineers, designers, architects, etc., require specific knowledge of the material such as the stress and strain the material is able to withstand before failing. Most materials exhibit rate-dependent properties and many applications expose materials to both low and high strain rate loading.

Various measurement devices have been developed for testing and quantifying the physical properties and stress characteristics of materials. For example, a Split-Hopkinson pressure bar may be used to test the dynamic stress-strain response of materials. During use of a Split-Hopkinson pressure bar, a specimen or test sample is placed between, and physically contacts, an incident bar and a transmission bar. At a first end of the incident bar away from the specimen, a stress wave, pressure wave, or incident wave is created using a striker bar. The incident wave propagates through the incident bar from the first end toward a second end that physically contacts the specimen. Upon reaching the specimen, a first portion of the energy from the incident wave travels through the specimen while a second portion is reflected away from the specimen and back through the incident bar. The first portion of the wave travels through, stresses, and deforms the specimen, and is then transferred to the transmission bar that physically contacts the specimen. Movement of the transmission bar may be stopped by a momentum bar and a momentum trap.

When the first and second portions of the incident wave reach the ends of the incident bar and the transmission bar respectively, the portions of the incident wave reflect off the ends of the bars and rapidly travel back and forth through the bars multiple times. Each time the incident wave reaches the specimen end of the bars, a portion of the incident wave energy is transferred to the specimen, which is again subjected to increased stresses. These transits of the incident wave back and forth through the incident bar and the transmission bar, and thus through the specimen, create a stepping motion and a non-constant strain rate in the specimen. A Split-Hopkinson pressure bar measurement is therefore valid only during the first motion step, but many materials will not have failed during that first motion step.

Additionally, the operational and failure characteristics of elastic materials such as vulcanizates (e.g., natural rubbers), elastomers (e.g., silicones, polymers), etc., are important considerations in selecting materials for use as sealers, barriers, vibration dampeners, shock absorbers and cushioners, as well as other uses. The Split-Hopkinson pressure bar subjects a test sample between the incident bar and the transmission bar to a compressive force as the incident wave travels through the test sample. The Split-Hopkinson pressure bar may thus test materials in tension, but does not function well for specimens that have a high strain to failure. Further, testing of a specimen using the Split-Hopkinson pressure bar subjects the material to a non-constant strain rate as the incident wave propagates back and forth through the incident bar and the transmission bar. The Split-Hopkinson pressure bar thus provides a high strain rate but not a high strain. Other devices using servo-mechanical methods may provide high strain but not a high strain rate.

A device that is suitable for measuring various characteristics such as tensile strength and failure stresses at a constant strain rate of various materials such as flexible, pliable, and ductile materials, as well as other materials, that provides both a high strain rate and high strain, would be a welcome addition to the art.

SUMMARY

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

An apparatus for measuring a dynamic tensile stress/strain response of a material includes a striker bar, a stretcher bar, a drive assembly configured to propel the striker bar toward the stretcher bar, and a stationary specimen mount configured to receive a first portion of a test sample and to maintain the first portion of the test sample in a fixed position. The apparatus further includes a movable specimen mount configured to receive a second portion of the test sample and to move away from the stationary specimen mount during a test or measurement of the test sample. In an embodiment, the striker bar is aligned with the stretcher bar, and the stretcher bar is configured to move away from the stationary specimen mount from an impact of the striker bar with the movable specimen mount. The striker bar may be configured to generate a pressure wave through the stretcher bar resulting from the impact of the striker bar with the movable specimen mount.

In an embodiment, the striker bar and the stretcher bar may be configured such that the pressure wave traverses from a first end of the stretcher bar to a second end of the stretcher bar and back to the first end of the stretcher bar. The striker bar and the stretcher bar may be further configured such that the pressure wave traverses from the first end of the stretcher bar into the striker bar during physical contact of the striker bar with the stretcher bar. Additionally, the striker bar and the stretcher bar may be configured to physically separate from each other after the pressure wave traverses from the first end of the stretcher bar into the striker bar, thereby trapping the pressure wave within the striker bar during the test or measurement of the test sample.

In an embodiment, the striker bar and the stretcher bar may be formed from a first material, the striker bar may have a first length, the stretcher bar may have a second length, and the first length may be longer than the second length. In another embodiment, the striker bar may be formed from a first material, the stretcher bar is formed from a second material that is different from the first material, and the first material and the second material are configured such that the pressure wave travels at a slower rate through the first material than through the second material.

The apparatus may further include a specimen mount support that receives the stationary specimen mount. The specimen mount support may include a first aperture therethrough and the stationary specimen mount may include a second aperture therethrough, and the striker bar may be configured to extend through the first aperture and the second aperture prior to impacting the movable specimen mount.

In an embodiment, the drive assembly may include a spring positioned within a channel assembly, and the spring may be configured to propel the striker bar toward the stretcher bar.

The stationary specimen mount may include a first groove therein configured to receive the first portion of the test sample. The movable specimen mount may include a second groove therein configured to receive the second portion of the test sample. At least one of the stationary specimen mount and the movable specimen mount may include a recess therein configured such that the test sample spans the recess during the test or measurement of the test sample.

The apparatus may further include a release assembly configured to maintain the striker bar in a ready position and to release the striker bar to initiate the test or measurement. The release assembly may include an electromagnet electrically coupled with a power source and the release assembly may be configured to maintain the striker bar in the ready position when the electromagnet is powered. Further, the release assembly may be configured to initiate the test or measurement upon removing power from the electromagnet.

A method for testing or measuring a test sample includes propelling a striker bar toward a stretcher bar, impacting a movable specimen mount with the striker bar, moving the movable specimen mount away from a stationary specimen mount resulting from the striker bar impacting the movable specimen mount, and applying a dynamic tensile stress and/or strain to a test sample attached to the stationary specimen mount and to the movable specimen mount resulting from the moving of the movable specimen mount away from the stationary specimen mount.

The method may further include generating a pressure wave within the stretcher bar resulting from the striker bar impacting the movable specimen mount, wherein the pressure wave traverses from a first end of the stretcher bar to a second end of the stretcher bar, and back to the first end of the stretcher bar. During physical contact of the striker bar with the movable specimen mount, the method may include transferring the pressure wave from the movable specimen mount into the striker bar and, after transferring the pressure wave from the movable specimen mount, physically separating the striker bar from the movable specimen mount to form a gap therebetween, thereby removing the pressure wave from the stretcher bar and trapping the pressure wave within the striker bar.

The method may further include propelling the striker bar toward the stretcher bar using a drive assembly. The striker bar may extend into an aperture through the stationary specimen mount prior to the impacting of the movable specimen mount with the striker bar.

The test sample may be prepared using a method including forming a rectangular strip of test material, adhering a support material to two or more edges of the rectangular strip of test material to provide a first attachment strip and a second attachment strip, placing the first attachment strip into a first groove in the stationary specimen mount, placing the second attachment strip into a second groove in the movable specimen mount, and positioning the test material over a recess formed by at least one of the stationary specimen mount and the movable specimen mount such that the test material spans the recess. The test material may be coated with a speckle pattern. In an embodiment, the applying of the dynamic tensile stress and/or strain to the test sample may apply a dynamic tensile strain of from 100 to 2500 strains per second to the test sample.

BRIEF DESCRIPTION OF THE DRAWINGS

The accompanying drawings, which are incorporated in and constitute a part of this specification, illustrate embodiments of the present teachings and together with the description, serve to explain the principles of the disclosure. In the figures:

FIG. 2 is a plan view depicting the FIG. 1 structure.

FIG. 3 is a side view depicting the FIG. 1 structure.

It should be noted that some details of the FIGS. have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same or like parts.

The present teachings provide a method and structure for testing and/or obtaining performance data on a test specimen such as an elastic or non-elastic material sample. The method may include the dynamic measurement of tensile strength of the material sample over a relatively constant strain rate. While some conventional measurement techniques propagate a pressure wave back and forth multiple times through various device structures as well as the test specimen, which results in a non-constant stress/strain on the test specimen, a device or test structure of the present teachings may, in some embodiments, have a decreased pressure wave propagation through various device structures and the test sample, thereby resulting in more accurate stress and/or strain data.

Figure 1:
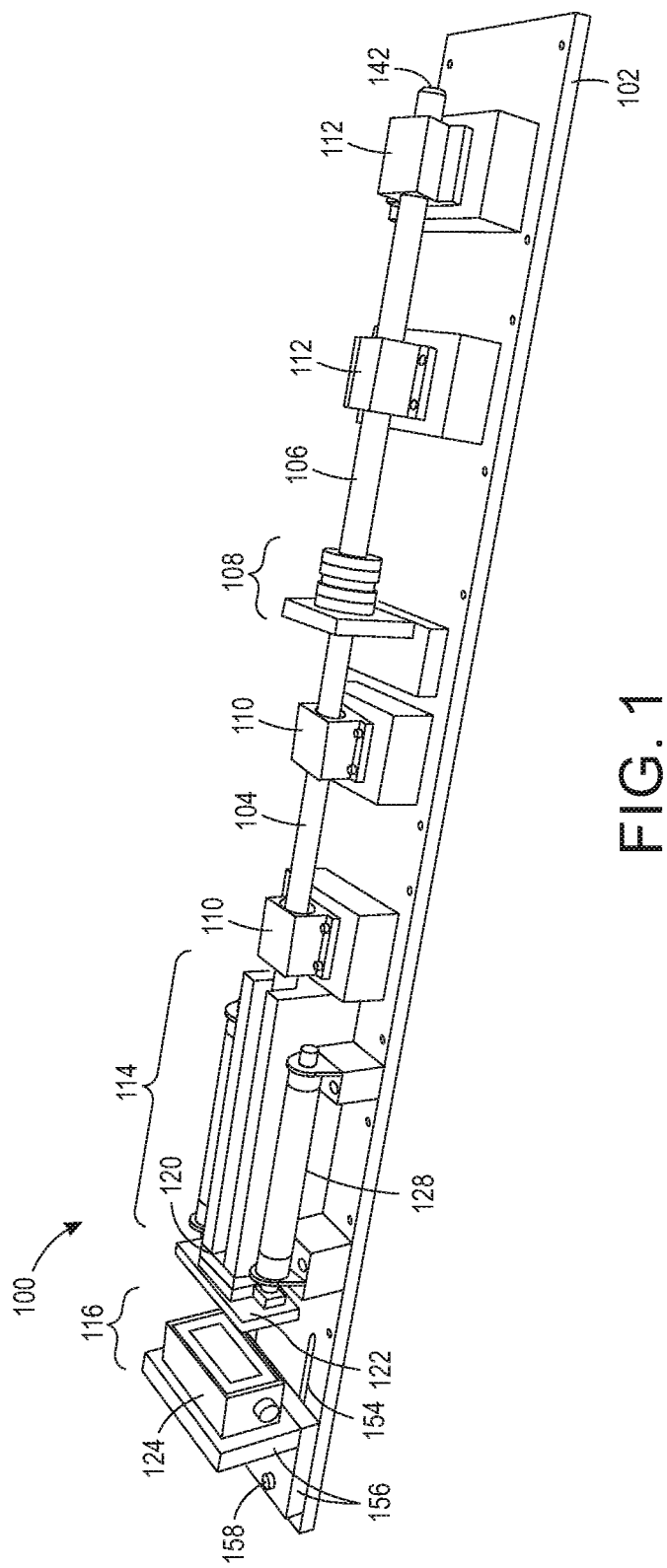
FIG. 1 is a perspective depiction of a device according to an embodiment of the present teachings that may be used to measure and test characteristics and responses of a specimen.

FIG. 1 is a perspective depiction, FIG. 2 is a plan view, and FIG. 3 is a side view, of a device or apparatus 100 for testing and/or measuring tensile characteristics, performance data, or other physical properties of a test sample. It will be appreciated that FIGS. 1-3 depict an exemplary structure, and that a measurement device in accordance with the present teachings may include other device substructures that are not depicted for simplicity, while various depicted device substructures may be removed or modified.

The device 100 may include a base 102 to which other measurement device substructures are attached and/or mounted using one or more fasteners, for example, one or more screws, bolts, pegs, clips, clamps, adhesives, etc. (not individually depicted for simplicity). The measurement device 100 further includes a striker bar 104, a stretcher bar 106, and a specimen mounting assembly 108.

The device 100 may further include one or more striker bar supports 110 attached to the base 102 that guide and support the striker bar 104, and allow axial movement of the striker bar 104 toward and away from the stretcher bar 106 during use. Each striker bar support 110 may include one or more bearings 500 (FIG. 5), such as one or more bushings (for example, solid sleeve bushings or split bushings), roller bearings, or other low-friction supports, that support and allow low-friction axial movement of the striker bar 104. Similarly, the device 100 may also include one or more stretcher bar supports 112 attached to the base 102 that guide and support the stretcher bar 106 and allow axial movement of the stretcher bar 106 away from the striker bar 104 during use. Each stretcher bar support 112 may include one or more bearings, such as one or more bushings (for example, solid sleeve bushings or split bushings), roller bearings, or other low-friction supports, that support and allow low-friction axial movement of the stretcher bar 106.

The device 100 of FIGS. 1-3 further includes a drive assembly 114 and a release assembly 116. The drive assembly 114 is configured to propel the striker bar 104 toward the stretcher bar 106 using, for example, one or more springs, compressed gas, or another method. The force with which the drive assembly 114 propels the striker bar 104 may be adjustable, for example, to accommodate different test sample materials and test conditions. The release assembly 116 is configured to maintain or hold the striker bar 104 in a ready, engaged, or cocked position and to release the striker bar 104 to initiate a test or measurement (hereinafter, collectively, "test") of the test sample. In a drive assembly 114 including a spring, the spring may be held under tension when the device 100 is in the ready position. In a drive assembly 114 including a fast acting gas valve, the gas may be pressurized within a canister when the device 100 is in the ready position. In addition to those described herein, other implementations of the drive assembly 114 and the release assembly 116, as well as other assemblies of the device 100, are contemplated.

The drive assembly 114 of the device 100 of FIGS. 1-3 includes a spring 118 that encircles the striker bar 104 and a retainer 120 attached to a first end 119 of the spring 118. A second end 121 of the spring 118 may be secured to the striker bar 104 within a channel assembly 123, where at least a portion of the spring 118 and a portion of the striker bar 104 are positioned and/or enclosed within a channel of the channel assembly 123. The drive assembly 114 may further include a plate 122 adjacent to the retainer 120. The plate 122 may be manufactured to be or include a ferromagnetic material such as an iron, an iron alloy, or another ferromagnetic material. In an embodiment, the plate 122 may be attached to a first end of the striker bar 104, and the first end of the striker bar 104 may extend through a hole in the retainer 120.

The release assembly 116 may include an electromagnet 124 attached to a power source 126. The electromagnet 124 is positioned such that the plate 122 may be held in the ready position by the electromagnet 124 after retracting the plate 122.

The device 100 may further include one or more retractors 128 to assist with retracting the drive assembly 114 from an idle position to the ready position. The retractors 128 retract the plate 122 away from the channel assembly 123 to position the plate 122, the spring 118, and the striker bar 104 into the ready position. The retractors 128 may include one or more electric, gas, or hydraulic pistons 128 in fluid communication with a power, gas, or hydraulic fluid source 130.

The specimen mounting assembly 108 may include a stationary specimen mount 132 and a movable specimen mount 134, each of which receives the specimen (i.e., the test sample) during a test. The stationary specimen mount 132 may be attached to a specimen mount support 136, while the movable specimen mount 134 may be attached to a first end of the stretcher bar 106. The specimen mounting assembly is described in more detail below with reference to FIGS. 4 and 5.

One or more data collection devices may be used to collect data during testing. The data collection devices may include, for example, a high-speed camera 140 focused, for example, on the specimen mounting assembly 108 during testing. Data collection may also including an accelerometer 142 positioned on a second end of the stretcher bar 106 or at another location suitable for monitoring a force and/or an acceleration of the stretcher bar 106 during testing.

The device 100 may be assembled such that the striker bar 104 is targeted to be in axial alignment with the stretcher bar 106. In other words, an axis of the striker bar 104 is aligned with an axis of the stretcher bar 106. To establish alignment of device 100 substructures, any number of spacers 150 may be positioned between the base 102 and one or more of the channel assembly 123, the striker bar supports 110, the specimen mount support 136, the stretcher bar supports 112, and/or at other locations as necessary or desired.

The base 102 may be a table or a surface secured to a table or other mounting surface. For most accurate test results, unintentional movement such as vibration of the device 100 may be minimized during testing. This includes vibrations and other unintentional movement resulting from external sources such as other equipment. Components and subassemblies of the device 100 may be manufactured from various materials such as polymers, metals such as steel or aluminum, and/or other natural or synthetic materials.

Figure 4:
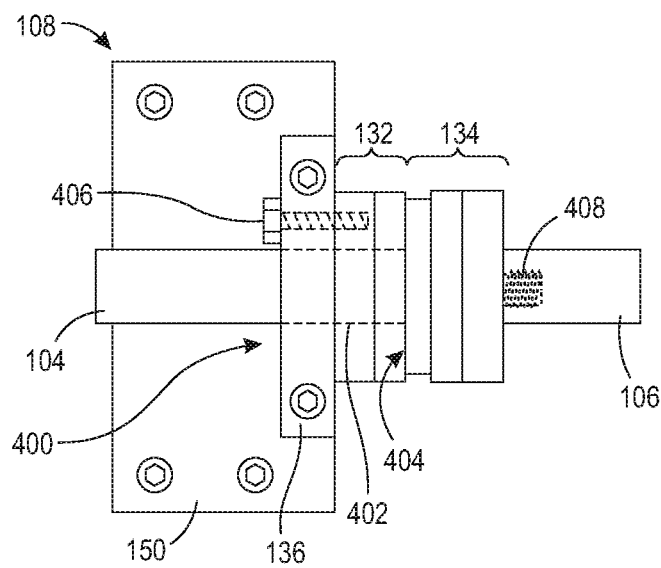
FIG. 4 is a transparent side view depicting a specimen mounting assembly according to an embodiment of the present teachings.
Figure 5:
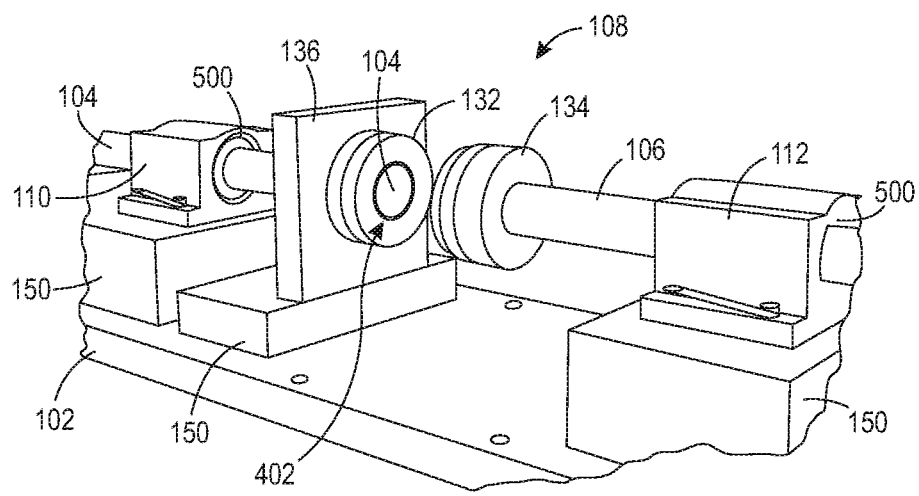
FIG. 5 is a perspective depiction including a specimen mounting assembly according to an embodiment of the present teachings.

FIG. 4 is a plan view, and FIG. 5 is a perspective depiction, of the device 100 in the region of the specimen mounting assembly 108. FIGS. 4 and 5 depict the device 100 in two different positions, but without a test sample affixed to the specimen mounting assembly 108. As depicted, the specimen mount support 136 includes an aperture 400 through which the striker bar 104 extends during a test. Additionally, the stationary specimen mount 132 also includes an aperture 402 through which the striker bar 104 extends during a test, where the aperture 400 is aligned with the aperture 402 to allow the passage of the striker bar 104 therethrough. The apertures 400, 402 allow the striker bar 104 to extend or pass through specimen mount support 136 and the stationary specimen mount 132 to physically contact an exposed face 404 of the movable specimen mount 134, and to propel the stretcher bar 106 and the attached movable specimen mount 134 during testing. FIG. 5 also depicts bearings 500 in the striker bar support 110 and the stretcher bar support 112 as described above.

As depicted, the stationary specimen mount may be removably or permanently mounted to the specimen mount support 136 using a fastener 406 such as one or more bolts or quick release fasteners. The movable specimen mount 134 may be removably or permanently mounted to the stretcher bar 106 using a fastener 408 such as one or more bolts or quick release fasteners. In another embodiment, the stationary specimen mount 132 and the specimen mount support 136 may be fabricated from a single piece of material, such that the stationary specimen mount 132 is part of the specimen mount support 136. Further, the stretcher bar 106 and the movable specimen mount 134 may be fabricated from a single piece of material, such that the movable specimen mount 134 is part of the stretcher bar 106.

Figure 6:
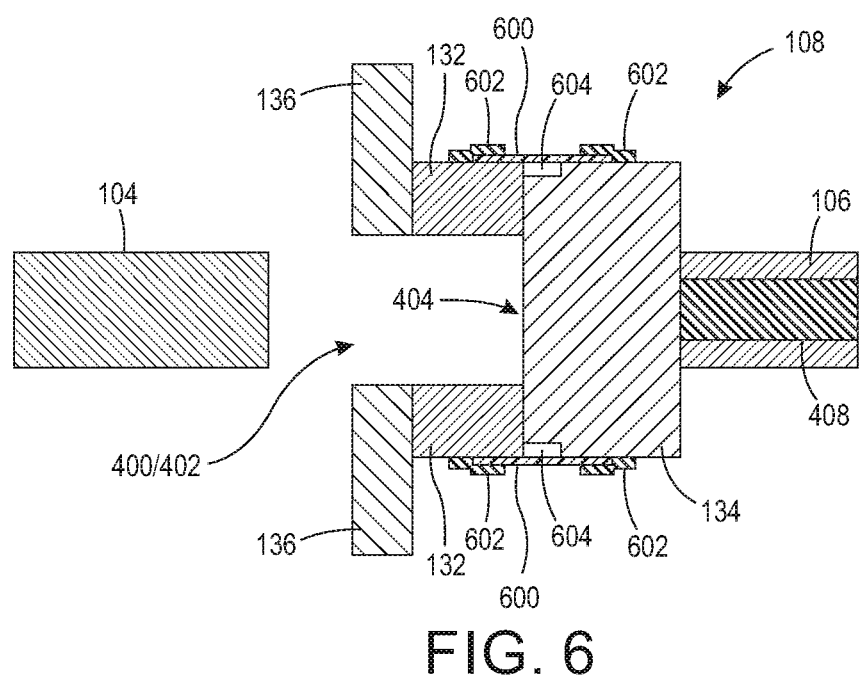
FIG. 6 is a side view depicting a specimen mounting assembly and a test sample according to an embodiment of the present teachings.

FIG. 6 is a cross section in the region of the specimen mounting assembly 108 with a test sample 600 mounted or attached to the stationary specimen mount 132 and the movable specimen mount 134 using one or more fasteners 602 such as tape, epoxy, clamps, etc. The test sample 600 may be, for example, a rectangular strip of flexible material that is wrapped at least partially, or completely, around the circumference of both the stationary specimen mount 132 and the movable specimen mount 134. As depicted in FIG. 6, the test sample 600 spans a recess 604 formed by one or both of the stationary specimen mount 132 and the movable specimen mount 134, such that a portion of the test sample 600 that spans the recess 604 is physically unsupported by stationary specimen mount 132 and the movable specimen mount 134. FIG. 6 depicts the specimen mounting assembly 108 prior to testing the test sample 600. The striker bar 104 is in the ready position, prior to striking the exposed face 404 of the movable specimen mount 134.

Figure 7:
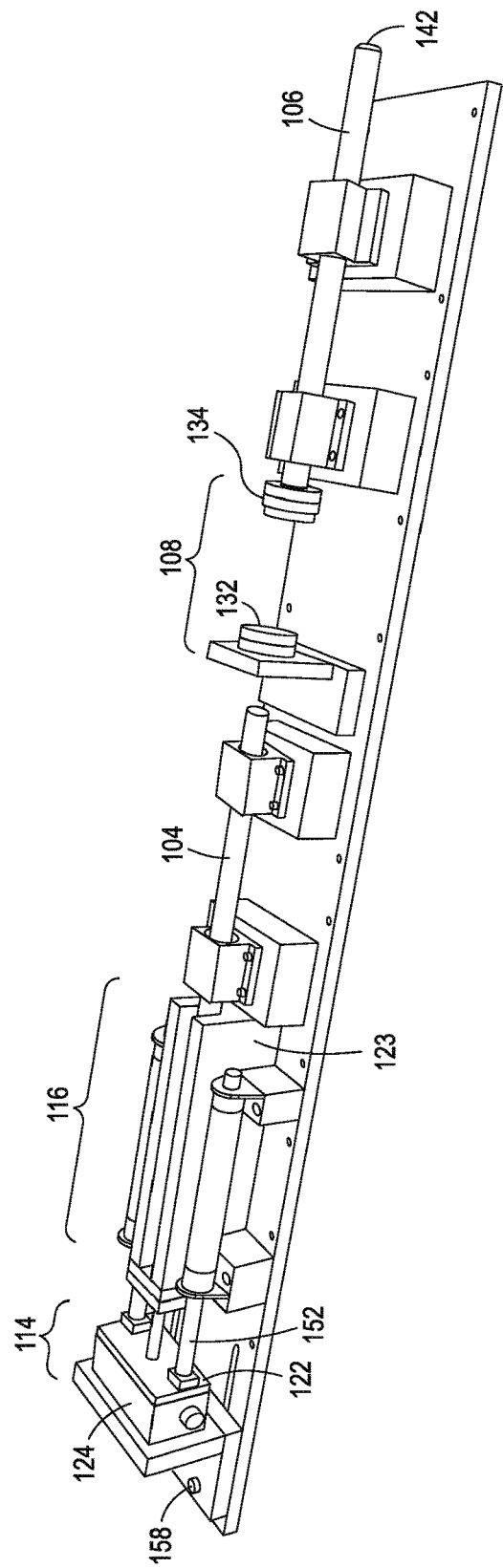
FIG. 7 is a perspective depiction of the FIG. 1 device in a ready position.

To perform a test, the device 100 if FIG. 1 is first placed into the ready position. In the embodiment depicted, the plate 122 is moved toward the electromagnet 124 by pressurizing the one or more gas pistons 128 using the gas source 130 to extend an arm 152 of each gas piston 128 such that the plate 122 engages or physically contacts the electromagnet 124 as depicted in FIG. 7. The electromagnet 124 is powered to maintain the plate 122 in the ready position, and the gas pistons 128 are depressurized to retract the arms 152 away from the plate 122. In this position, a potential energy is imparted to the spring 118 within the channel assembly 123.

For purposes of illustration, FIG. 7 depicts the movable specimen mount 134 positioned away from the stationary specimen mount 132, with no test specimen positioned within the specimen mounting assembly 108. Typically, prior to positioning the device 100 in the ready position, a test sample 600 will be positioned within the specimen mounting assembly 108 as depicted in FIG. 6.

Figure 8:
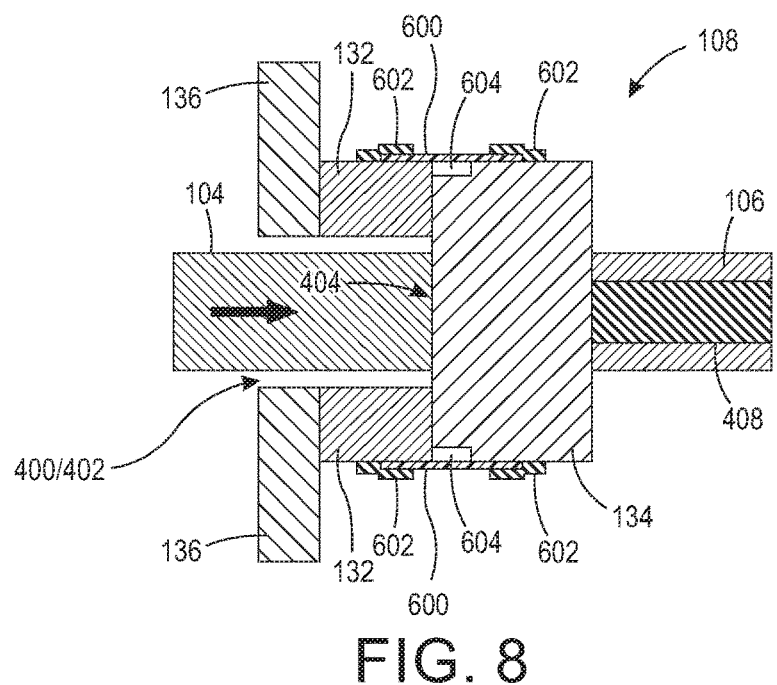
FIG. 8 is a side view of the FIG. 6 structure as the striker bar contacts the movable specimen mount.

After placing the test sample 600 into the specimen mounting assembly 108 of device 100 and positioning the device 100 into the ready position, a test may be initiated by removing power from the electromagnet 124. The potential energy imparted to the spring 118 is released and converted to kinetic energy, which propels the striker bar 104 toward the stretcher bar 106. During the testing phase, a second end of the striker bar 104 may extend into the aperture 400 through the specimen mount support 136, and into the aperture 402 through the stationary specimen mount 132, to physically contact the exposed face 404 of the movable specimen mount 134. FIG. 8 depicts the striker bar 104 just as it makes contact with the face 404 of the movable specimen mount 134.

Figure 9:
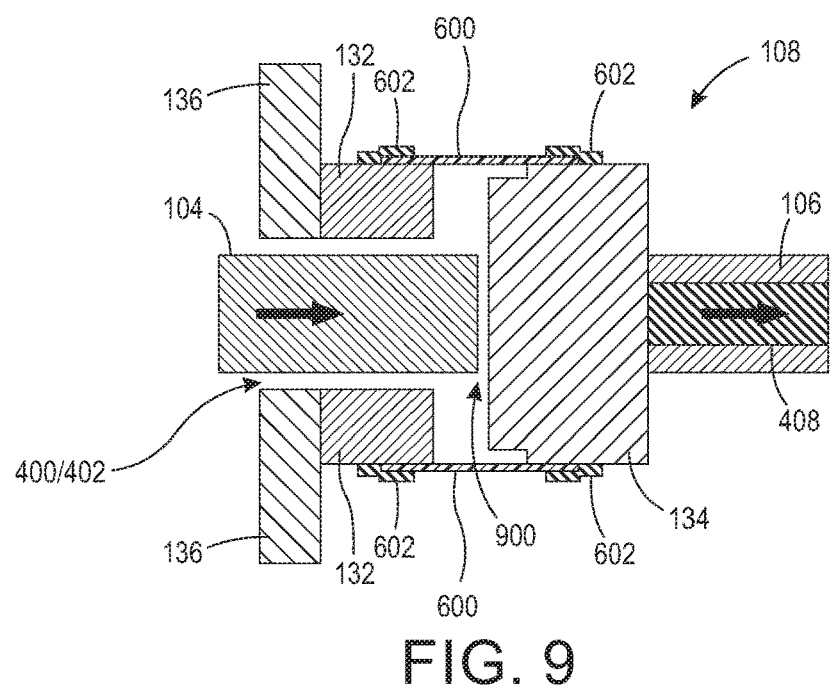
FIG. 9 is a side view of the FIG. 8 structure after impact of the movable specimen mount by the striker bar, and during exposure of the test sample to a tensile stress and/or stain.

Subsequently, energy from the striker bar 104 is transferred to the movable specimen mount 134 that is attached to the stretcher bar 106, and the stretcher bar 106 and movable specimen mount 134 are propelled away from the stationary specimen mount 132, for example, as depicted in FIG. 9. Movement of the movable specimen mount 134 away from the stationary specimen mount 132 thereby places a tensile stress and tensile strain on the test sample 600 as depicted. If the striker bar 104 is propelled with sufficient force, the test sample 600 may partially or completely fail from the tensile stress or strain.

The force the striker bar 104 places on the exposed face 404 of the movable specimen mount 134 may be increased, for example, by using a spring 118 with a higher compression force spring (i.e., a stiffer spring) and/or by moving the electromagnet 124 further away from the channel assembly 123 such that the spring 118 is placed under a higher potential energy in the ready position. In an embodiment, the base 102 may include one or more slots 154 that receive one or more adjustment bolts 156 through an electromagnet mount 158. The adjustment bolts 156 may be loosened for repositioning of the electromagnet mount 158 and the electromagnet 124 attached to the electromagnet mount 158, and then tightened to secure the electromagnet mount 158 and the electromagnet 124.

During testing of the test sample, data may be collected by any number of desired data collection devices such as the high-speed camera 140 and/or the accelerometer 142.

When the striker bar 104 contacts the movable specimen mount 134, a pressure wave is generated that propagates through the movable specimen mount 134 and into the stretcher bar 106. When the pressure wave reaches the second end of the stretcher bar 106 (i.e., the end opposite the movable specimen mount 134), it reflects off the second end and propagates back through the stretcher bar 106 and the movable specimen mount 134. As described above, in the Split-Hopkinson pressure bar, the pressure wave continues to propagate back and forth multiple times through the bars and the test sample, thereby creating a non-continuous stress and non-continuous strain within and through the test sample. In contrast to the operation of the Split-Hopkinson pressure bar, the striker bar 104 and the stretcher bar 106 of device 100 may be designed to provide a more continuous stress on the test sample 600.

In an embodiment, the striker bar 104 and the stretcher bar 106 of the device 100 may be designed or selected to trap the pressure wave within the striker bar 104 after only one cycle of the pressure wave through the stretcher bar 106. Upon initial contact between the striker bar 104 and the stretcher bar 106 as depicted in FIG. 8, a first pressure wave is generated that propagates through the stretcher bar 106 to the second (opposite) end of the stretcher bar 106, and reflects off the second end back to the first end. Similarly, upon this initial contact, a second pressure wave is generated that propagates through the striker bar 104 to the first (opposite) end of the striker bar 104, and reflects off the first end back to the second end.

During the traversal of the first pressure wave through the stretcher bar 106, the striker bar 104 remains in physical contact with the exposed face 404. Once the first pressure wave returns to the first end of the stretcher bar 106, the first pressure wave enters the striker bar 104. At this point, the striker bar 104 and the stretcher bar 106 separate as depicted in FIG. 9 such that there is a gap 900 between the second end of the striker bar 104 and the exposed face 404 of the movable specimen mount 134 such that, when the first pressure wave reflects off the first end of the striker bar 104 and returns to the second end of the striker bar 104, the first pressure wave cannot reenter the stretcher bar 106. Similarly, the second pressure wave cannot enter the stretcher bar 106. The gap 900 remains until after the test of the test sample 600 is completed. Thus, in contrast to the Split-Hopkinson pressure bar that subjects the test sample to the pressure wave multiple times, the test sample 600 is subjected to the pressure wave fewer times, thereby imparting a more continuous stress to the test sample during testing. In contrast, the Split-Hopkinson pressure bar has a wave that continues to propagate and reflect through the test device and the test specimen. This creates a step motion and a non-constant strain. For at least this reason, a Split-Hopkinson pressure bar measurement is valid only during the first step.

In an embodiment, when the striker bar 104 impacts the stretcher bar 106 a compression wave is generated in both bars 104, 106. The compression waves propagate out from the impact location. When the compression waves reach the opposite ends of the each bar 104, 106, the compression waves reflect as a tension wave moving back toward the interface between the two bars 104, 106 (i.e., toward the test sample 600). The net result is that the tension wave and oncoming compression wave combine to produce zero net stress. However, when the tension wave from the striker bar 104 and the tension wave from the stretcher bar 106 meet, the tension waves combine to form a net tensile stress. If the striker bar 104 and the stretcher bar 106 are of equal length, the tensile stress first forms at the interface between the two bars 104, 106. The interface cannot support tension, so the bars 104, 106 separate. In this case, the stretcher bar 106 is then left with a stress wave that continues propagating and reflecting through the stretcher bar 106. This wave transit causes the stretcher bar 106 to have an undesirable step-motion and thus a non-constant strain in the test specimen 600. However, if the stretcher bar 106 is shorter than the striker bar 104, the reflected tension waves meet and combine within the striker bar 104. When this tension wave reaches the interface between the two bars 104, 106, the tension wave causes separation of the two bars 104, 106 thereby trapping the waves within the striker bar 104, leaving the stretcher bar 106 with a smooth linear motion.

In an embodiment, the striker bar 104 and the stretcher bar 106 may be manufactured from the same material, for example, stainless steel, aluminum, other metals or metal alloys, or another suitable material. In this embodiment, pressure waves travel through both the striker bar 104 and the stretcher bar 106 at the same rate. The timing of contact between the striker bar 104 and the stretcher bar 106 (i.e., "contact timing") may be selected by providing a striker bar 104 having a first length and a stretcher bar 106 (including the movable specimen mount 134) having a second length, where the first length is longer than the second length. In this embodiment, the first pressure wave traverses the stretcher bar 106 and enters the striker bar 104 before the second wave traverses the striker bar 104 because the second wave in the striker bar 104 has a longer distance to travel. Before the second wave reaches the second end of the striker bar 104, striker bar 104 and stretcher bar 106 separate to form the gap 900.

In another embodiment, the striker bar 104 may be manufactured from a first material and the stretcher bar 106 may be manufactured from a second material, where the first material propagates a pressure wave at a slower rate or slower speed than the second material. Thus, in this embodiment, the striker bar 104 and the stretcher bar 106 may have the same length and the contact timing is controlled by the materials from which the bars are formed. In this embodiment, the striker bar 104 may be formed from brass while the stretcher bar 106 is formed from steel, where the wave speed in steel is approximately 1.7 times that of brass. The contact timing itself may thus be similar to that as described above, such that the first and second pressure waves are trapped within the striker bar 104 when the two bars 104, 106 separate and the gap 900 occurs. In any case, the materials selected such that the striker bar 104 and the stretcher bar 106 do not deform on impact, or so that any error in measurement of the sample 600 resulting from deformation is within acceptable tolerances.

Figure 10:
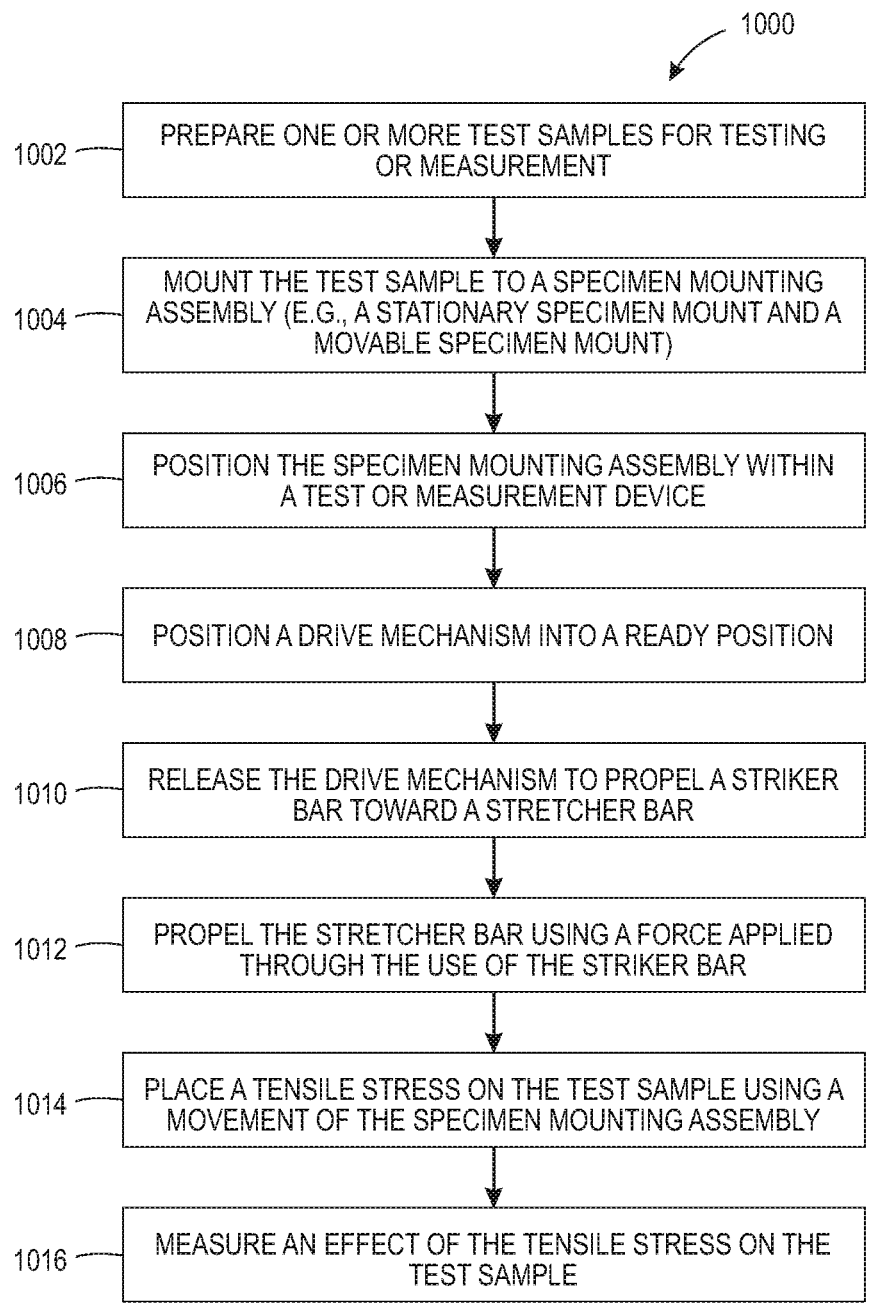
FIG. 10 is a flow chart of a method for testing or measuring a test sample according to an embodiment of the present teachings.

FIG. 10 is a flow chart depicting an exemplary method 1000 for testing or measuring a test sample according to an embodiment of the present teachings. It will be understood that the described method is an example method. When implemented, an method according to the present teachings may include fewer or additional processing stages than those described and/or depicted, and the described processing stages may be implemented in a different order than described herein. In addition, the method 1000 may proceed by operation of one or more portions of the apparatus of FIGS. 1-9, 11, and 12, and is thus described by reference thereto. However, it will be appreciated that the method 1000 is not limited to any particular structure unless otherwise expressly stated.

In an embodiment, one or more test samples may be prepared for measurement as depicted at 1002. The test sample may be an elastic material, for example, a silicone or other polymer, or the test sample may be a solid such as a ceramic, a metal, a metal alloy, a natural or synthetic composite, etc. In an embodiment, a sheet of test material may be prepared, for example, by dispensing a liquid or gel to a uniform or non-uniform thickness. The test material may be cured using thermal processing, ultraviolet light, or another suitable process. The test material may be formed, molded, cut, etc., into a desirable shape for testing. For example, a sheet of test material may be sectioned into a plurality of test samples, such as a plurality of rectangular strips. In an embodiment, a solid material may be, for example, pressed or stamped into a sheet, or drawn into a wire, for testing. A test sample may include a single layer of material, or two or more layers of one or more materials.

Figure 11:
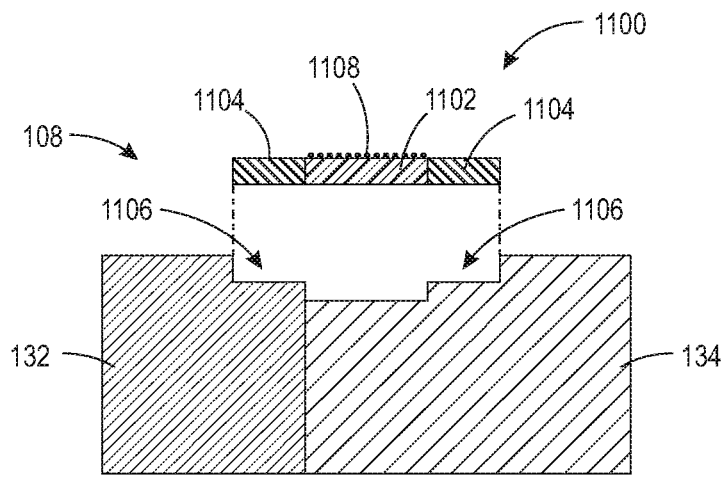
FIG. 11 is a side view of a test sample, a stationary specimen mount, and a movable specimen mount according to an embodiment of the present teachings.

In an embodiment, the test sample may be prepared by forming one or more rectangular strips of a test material. For example, FIG. 11 is an exploded magnified cross section of part of a specimen mounting assembly 108, and depicts a test sample 1100. The cross section of FIG. 11 is a section through a width of the test sample 1100, and the test sample 1100 may extend around a circumference of both the stationary specimen mount 132 and the movable specimen mount 134 partially or completely. The test sample 1100 may include a test material 1102 as well as a support material such as an epoxy, another synthetic or natural adhesive, or other support material adhered to two or more edges of the test material 1102 to provide attachment strips 1104. Tensile adhesion of the attachment strips 1104 to the test material 1102 should exceed the tensile stress at which the test material 1102 fails to prevent separation of the attachment strips 1104 from the test material 1102 during the test or measurement. Further, tensile strength of the attachment strips 1104 should exceed the tensile strength of the test material 1102 to prevent failure of the attachment strips 1104 prior to failure of the test material 1102. In an embodiment, the attachment strips 1104 are sized and configured to fit within test sample grooves 1106 formed within and around the circumference of the stationary specimen mount 132 and the movable specimen mount 134. The stationary specimen mount 132 thereby receives a first portion of the test sample 1100 and maintains the first portion of the test sample in a fixed position during the test or measurement. Further, the movable specimen mount 134 thereby receives a second portion of the test sample 1100 and moves away from the stationary specimen mount 132 during the test or measurement of the test sample 1100. In an embodiment, preparation of the test sample 1100 may include coating the test material 1102 with a speckle pattern 1108 for use with, for example, digital image correlation. The speckle pattern 1108 may include, for example, a light-reflective polymer, a metal flake such as a silver flake, or another light-reflective material.

Figure 12:
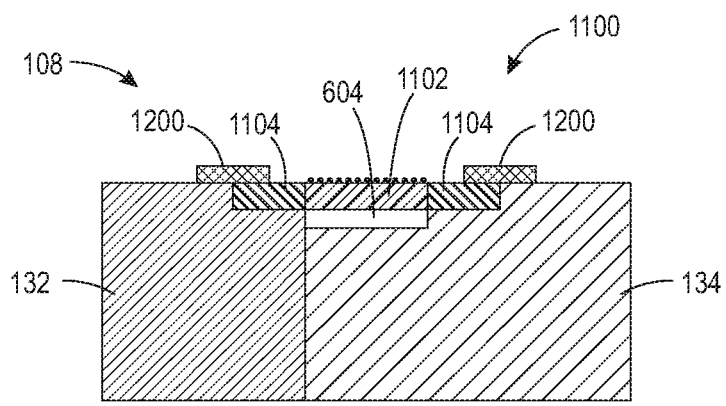
FIG. 12 is a side view of the FIG. 11 structure after attaching the test sample.

As depicted at 1004, the test sample is mounted to the specimen mounting assembly. This may include, for example, positioning the attachment strips 1104 within the test sample grooves 1106 as depicted in FIG. 12. The test sample 1100 may be attached to the specimen mounting assembly 108 using one or more fasteners 1200, such as one or more adhesives, tape strips, epoxies, or other fastener 1200. As depicted in FIG. 12, the test material 1102 spans the recess 604 formed by one or both of the stationary specimen mount 132 and the movable specimen mount 134, such that at least a portion of the test material 1102 spans the recess 604 and is physically unsupported by stationary specimen mount 132 and the movable specimen mount 134. The specimen mounting assembly 108 depicted and described above is merely one design of mounting assembly, and others are contemplated.

In an embodiment, a method may include attaching the test sample to the specimen mounting assembly (or subassembly) at a location that is remote from the remainder of the device 100, and then the specimen mounting assembly may be subsequently attached to the remainder of the device 100 as depicted at 1006.

Next, the drive assembly 114 may be moved from a resting or idle position to a cocked or ready position as depicted at 1008. In the device 100 of FIG. 2, this may include filling the gas pistons 128 with gas from the gas source 130 to extend the arms 152, thereby moving the plate 122 into position against the electromagnet 124. When power from the power source 126 is engaged, the plate 122 is held against the electromagnet 124 using magnetism, which maintains the drive assembly 114, including the spring 118, in the ready position. The drive assembly 114 depicted and described above is merely one possible drive assembly, and other electrical, mechanical, electromechanical, pneumatic, and chemical drive assemblies are contemplated.

After placing the drive assembly 114 into the ready position, the drive assembly 114 is released or fired as depicted at 1010 to initiate a test or measurement. In the device of FIG. 2, for example, power may be removed from the electromagnet 124, thereby releasing the plate 122 and the spring 118. The drive assembly 114 thereby propels the stretcher bar 106 toward the striker bar 104 using the force applied by the spring 118 as depicted at 1012. The striker bar 104 extends through the aperture 400 in the specimen mount support 136 and the aperture 402 in the stationary specimen mount 132 to impact the exposed face 404 of the movable specimen mount 134. This causes a physical separation of the stationary specimen mount 132 and the movable specimen mount 134, and places a tensile stress on the test sample using a movement of the specimen mounting assembly as depicted at 1014. During the tensile stress, the effects of the tensile stress may be measured as depicted at 1016 using, for example, a high-speed camera 140, an accelerometer 142, or another measurement technique. In an embodiment, images from the high-speed camera 140 may capture the specimen 600, and particularly the speckle pattern 1108. Digital image correlation (DIC) may be used to calculate strain within the specimen 600. For example, the high-speed video frames may be post processed using particle image velocimetry (PIV) techniques to allow tracking of, for example, the speckle pattern 1108 and calculation of strain of the sample 600.

Thus an embodiment of the present teachings may include a device or apparatus for measuring dynamic stress/strain response of ductile materials, elastic materials, or other materials. When measuring dynamic strength, constant rate loading is an important factor in obtaining accurate test or measurement results. In contrast to conventional devices such as the Split-Hopkinson pressure bar which has a relatively short impactor bar, a transmitting bar, and a receiving bar, a device in accordance with the present teachings may include only a striker and a stretcher bar. In an embodiment, a pressure wave or pressure wave requires a longer time to travel through the striker bar than the stretcher bar, for example, by forming the striker bar to have a longer length than the stretcher bar or by forming the striker bar that propagates the pressure wave at a slower rate than the striker bar. As a result, after impact of the striker bar with the stretcher bar, the two bars stay in contact long enough for the pressure wave to reflect off the far end of the stretcher and run back into the striker. At this point, while the wave is in the striker bar, the bars separate leaving the stretcher bar with smooth forward motion until the specimen fails. Servo-hydraulic test frames work well at low strain rates but are unable to provide high stain rate loading. In an embodiment of the present teachings, the device 100 may provide strain rate loading of above 2 strains per second, for example, in the range of about 100 to about 2500 strains per second. While the Split-Hopkinson pressure bar works well with brittle materials, it is not able to provide a constant strain rate over a large distance and, for at least this reason, is not appropriate for testing highly ductile materials to the point of failure.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

The invention claimed is:

1. An apparatus for measuring a dynamic tensile stress/strain response of a material, comprising:
   a base;
   a striker bar supported by a base;
   a stretcher bar supported by the base;
   a drive assembly supported by the base and configured to propel the striker bar toward the stretcher bar;
   a stationary specimen mount supported by the base and configured to receive a first portion of a test sample and to maintain the first portion of the test sample in a fixed position; and
   a movable specimen mount attached to the stretcher bar and configured to receive a second portion of the test sample and to move away from the stationary specimen mount during a test or measurement of the test sample,
   wherein the striker bar is aligned with the stretcher bar, and the stretcher bar is configured to move away from the stationary specimen mount from an impact of the striker bar with the movable specimen mount.

2. The apparatus of claim 1, wherein:
   the striker bar is configured to generate a pressure wave through the stretcher bar resulting from the impact of the striker bar with the movable specimen mount;
   the striker bar and the stretcher bar are configured such that the pressure wave traverses from a first end of the stretcher bar to a second end of the stretcher bar and back to the first end of the stretcher bar;
   the striker bar and the stretcher bar are configured such that the pressure wave traverses from the first end of the stretcher bar into the striker bar during physical contact of the striker bar with the stretcher bar; and
   the striker bar and the stretcher bar are configured to physically separate from each other after the pressure wave traverses from the first end of the stretcher bar into the striker bar, thereby trapping the pressure wave within the striker bar during the test or measurement of the test sample.

3. The apparatus of claim 2, wherein:
   the striker bar is formed from a first material;
   the stretcher bar is formed from the first material;
   the striker bar has a first length;
   the stretcher bar has a second length; and
   the first length is longer than the second length.

4. The apparatus of claim 2, wherein:
   the striker bar is formed from a first material;
   the stretcher bar is formed from a second material that is different from the first material; and
   the first material and the second material are configured such that the pressure wave travels at a slower rate through the first material than through the second material.

5. The apparatus of claim 1, further comprising a specimen mount support that receives the stationary specimen mount.

6. The apparatus of claim 5, wherein the specimen mount support comprises a first aperture therethrough and the stationary specimen mount comprises a second aperture therethrough, and the striker bar is configured to extend through the first aperture and the second aperture prior to impacting the movable specimen mount.

7. The apparatus of claim 6, wherein:
   the drive assembly comprises a spring positioned within a channel assembly; and
   the spring is configured to propel the striker bar toward the stretcher bar.

8. The apparatus of claim 1, wherein:
   the stationary specimen mount comprises a first groove therein configured to receive the first portion of the test sample;
   the movable specimen mount comprises a second groove therein configured to receive the second portion of the test sample; and
   at least one of the stationary specimen mount and the movable specimen mount comprises a recess therein configured such that the test sample spans the recess during the test or measurement of the test sample.

9. The apparatus of claim 1, further comprising a release assembly configured to maintain the striker bar in a ready position and to release the striker bar to initiate the test or measurement.

10. The apparatus of claim 9, wherein:
the release assembly comprises an electromagnet electrically coupled with a power source;
the release assembly is configured to maintain the striker bar in the ready position when the electromagnet is powered; and
the release assembly is configured to initiate the test or measurement upon removing power from the electromagnet.

11. The apparatus of claim 1, further comprising:
at least one first spacer attached to the base;
at least one striker bar support attached to the at least one first spacer such that the striker bar is supported by the base through the at least one striker bar support and the at least one first spacer;
at least one second spacer attached to the base; and
at least one stretcher bar support attached to the at least one second spacer such that the stretcher bar is supported by the base through the at least one stretcher bar support and the at least one second spacer.

12. A method for testing or measuring a test sample, comprising:
mounting the test sample to a stationary specimen mount;
mounting the test sample to a movable specimen mount;
with the movable specimen mount attached to a stretcher bar, propelling a striker bar toward the stretcher bar;
impacting the movable specimen mount with the striker bar;
with the test sample mounted to the stationary specimen mount and to the movable specimen mount, moving the movable specimen mount away from the stationary specimen mount resulting from the striker bar impacting the movable specimen mount; and
applying a dynamic tensile stress and/or strain to the test sample mounted to the stationary specimen mount and to the movable specimen mount, the dynamic tensile stress and/or strain resulting from the moving of the movable specimen mount away from the stationary specimen mount.

13. The method of claim 12, further comprising:
generating a pressure wave within the stretcher bar resulting from the striker bar impacting the movable specimen mount, wherein the pressure wave traverses from a first end of the stretcher bar to a second end of the stretcher bar, and back to the first end of the stretcher bar;
during physical contact of the striker bar with the movable specimen mount, transferring the pressure wave from the movable specimen mount into the striker bar; and
after transferring the pressure wave from the movable specimen mount, physically separating the striker bar from the movable specimen mount to form a gap therebetween, thereby removing the pressure wave from the stretcher bar and trapping the pressure wave within the striker bar.

14. The method of claim 13, further comprising propelling the striker bar toward the stretcher bar using a drive assembly.

15. The method of claim 14, further comprising extending the striker bar into an aperture through the stationary specimen mount prior to the impacting of the movable specimen mount with the striker bar.

16. The method of claim 12, further comprising preparing the test sample using a method comprising:
forming a rectangular strip of test material;
adhering a support material to two or more edges of the rectangular strip of test material to provide a first attachment strip and a second attachment strip;
placing the first attachment strip into a first groove in the stationary specimen mount;
placing the second attachment strip into a second groove in the movable specimen mount; and
positioning the test material over a recess formed by at least one of the stationary specimen mount and the movable specimen mount such that the test material spans the recess.

17. The method of claim 16, further comprising coating the test material with a speckle pattern.

18. The method of claim 12, wherein the applying of the dynamic tensile stress and/or strain to the test sample applies a dynamic tensile strain of from 100 to 2500 strains per second to the test sample.

19. A method for testing or measuring a test sample, comprising:
propelling a striker bar toward a stretcher bar;
impacting a movable specimen mount with the striker bar;
moving the movable specimen mount away from a stationary specimen mount resulting from the striker bar impacting the movable specimen mount; and
applying a dynamic tensile stress and/or strain of from 100 to 2500 strains per second to a test sample, wherein the test sample is attached to the stationary specimen mount and to the movable specimen mount, wherein the dynamic tensile stress and/or strain results from the moving of the movable specimen mount away from the stationary specimen mount.

20. The method of claim 19, further comprising extending the striker bar into an aperture through the stationary specimen mount prior to the impacting of the movable specimen mount with the striker bar.

* * * * *